US006846458B1

(12) United States Patent
Staphanos (10) Patent No.: US 6,846,458 B1
(45) Date of Patent: Jan. 25, 2005

(54) PROCESS ANALYTIC SYSTEM WITH IMPROVED SAMPLE HANDLING SYSTEM

(75) Inventor: Stephen Staphanos, Long Beach, CA (US)

(73) Assignee: Rosemount Analytical Inc., Anaheim, CA (US)

( * ) Notice: Subject to any disclaimer, the term of this patent is extended or adjusted under 35 U.S.C. 154(b) by 695 days.

(21) Appl. No.: 09/430,469

(22) Filed: Oct. 29, 1999

(51) Int. Cl.[7] .............................................. G01N 35/00
(52) U.S. Cl. ........................................ 422/81; 422/62
(58) Field of Search .......................... 422/62, 81, 68.1, 422/83, 89, 94; 436/167; 73/23.2, 23.35, 23.4, 23.41; 702/22, 32

(56) References Cited

U.S. PATENT DOCUMENTS

| | | | | |
|---|---|---|---|---|
| 4,229,971 A | | 10/1980 | Ririe, Jr. ..................... 73/61 R |
| 4,345,463 A | * | 8/1982 | Wilson et al. ................ 73/190 |
| 4,359,891 A | * | 11/1982 | Ahlstrom, Jr. et al. ....... 73/23.1 |
| 4,911,891 A | | 3/1990 | Platt .......................... 422/68.1 |
| 5,610,835 A | * | 3/1997 | Dominguez et al. ........ 364/497 |
| 5,741,960 A | * | 4/1998 | Payne et al. ............... 73/23.41 |
| 5,756,360 A | * | 5/1998 | Harvey et al. .............. 436/179 |
| 6,004,514 A | * | 12/1999 | Hikosaka et al. ............. 422/89 |

FOREIGN PATENT DOCUMENTS

WO    WO 97/12239 A1 * 4/1997

OTHER PUBLICATIONS

Author unknown, GCX Manual on the HMI Software, 7/99.*
GCX Transmitter, The Next Generation Process Gas Chromatograph, 6 pages (1997).*
Chromatography, downloaded from http://www.frco.com/proanalytic/products/chroma.html, 1 page, (Oct. 24, 1999).
Combustion Analyzers, downloaded from http://www.frco.com/proanalytic/products/comb_analyzers.html, 8 pages, (Oct. 24, 1999).
Oxygen (02) Analyzers, downloaded from http://www.frco.com/proanalytic/products/oa.html, 8 pages, (Oct. 24, 1999).

* cited by examiner

Primary Examiner—Jill Warden
(74) Attorney, Agent, or Firm—Westman, Champlin & Kelly, P.A.

(57) ABSTRACT

A process analytic system provides communication between a process analyzer and process sample handling system. The communication allows the process analyzer to modify at least one parameter of the sample handling system to facilitate quick and efficient setup, calibration, and maintenance of the process analytic system. The process analytic system includes a sample handling system that is coupled to a process analyzer to provide a process sample to the process analyzer, and to communicate with the process analyzer. The process analyzer can command the sample handling system to modify at least one sample handling parameter. The process analyzer can modify sample handling parameters based upon sample analysis, diagnostics of the sample handling system, or both.

24 Claims, 4 Drawing Sheets

PROCESS ANALYTIC SYSTEM WITH IMPROVED SAMPLE HANDLING SYSTEM

BACKGROUND OF THE INVENTION

Process analytic systems are used in a variety of industries to measure process characteristics in substantially real-time. Such industries include the chemical, petrochemical, pipeline, and pharmaceutical industries. Process analytic systems are often used for process gas analysis, combustion analysis and control, and emissions monitoring in any of the above industries.

Process analytic systems differ substantially from laboratory analyzers in the manner in which sample handling is effected. For example, samples are usually held as a gas or liquid in an appropriate container that is transported, sometimes by hand, to a laboratory analytical instrument. In contrast, the process analytic system receives its sample directly from a sampling point in the process, without human assistance. Process analytic systems can include a process analyzer and a process sample handling system.

For a process analyzer in a process analytic system, such as a process gas chromatograph, to provide an accurate analysis of the process, it is important to convey the sample from the process to the analyzer such that the sample is representative of the process. Since any number of variables can affect the extent to which the sample represents the process, it is desirable to control many variables including temperature, pressure and flow while conveying the sample to the analyzer. Further complicating matters is the fact that the sample may be quite hot and under considerable pressure, contain water vapor, solids, condensed liquid, etc. One example of a known process analyzer is the Continuous Analyzer Transmitter, available from Rosemount Analytical, Inc., of Anaheim, Calif. Another example of a known process analyzer is the Model GCX Process Gas Chromatograph, available from Rosemount Analytical, Process Analytic Division, of Orrville, Ohio.

A process sample handling system is utilized in a process analytic system to extract a process sample from a sampling point and convey the sample to a process analyzer. Generally, the sample handling system includes all requisite components to maintain a constant sample flow to the analyzer. Thus, the sample handling system generally includes suitable pressure reduction components, filters, vaporizers, flow controls, and sample switching or selector valves for introducing multiple sample streams or a calibration standard to the process analyzer. With the exception of vaporizers, filters, and pressure reducers, most components of the sample handling system are usually located near the process analyzer, and sometimes within the same housing as the analyzer.

The process sample handling system is an important component of an effective process analytic system. If the process sample is not delivered to the process analyzer in a condition that is representative of the process, errors will occur in the analysis. Many of the problems encountered in process analytic systems can be traced to a problem occurring in the process sample handling system.

Individual process applications are each relatively unique. The combination of process fluid pressure, temperature, flow, chemistry and other factors contribute to the uniqueness of a given process. In order to facilitate effective process analysis, process sample handling systems have been designed for specific process applications. This is done once information about a specific process application is known. Although such specific tailoring reduces error in the process analytic system, it requires additional manufacturing time since a custom system must be built for each application. Additionally, significant field installation time is generally required for system commissioning.

As industrial process analysis and control becomes more sophisticated there is an increasing need to provide a process sample handling system for a process analytic system that does not need to be manually customized, either by manufacturing or by commissioning, for each application.

SUMMARY

A process analytic system provides communication between a process analyzer and process sample handling system. The communication allows the process analyzer to modify at least one parameter of the sample handling system to facilitate quick and efficient setup, calibration, and maintenance of the process analytic system.

The process analytic system includes a sample handling system that is coupled to a process analyzer to provide a process sample to the process analyzer, and to communicate with the process analyzer. The process analyzer can command the sample handling system to modify at least one sample handling parameter. The process analyzer can modify sample handling parameters based upon sample analysis, diagnostics of the sample handling system, or both.

DETAILED DESCRIPTION

Although the present invention will be described with reference to specific embodiments of a process analytic system, workers skilled in the art will recognize that changes may be made in form and detail without departing from the spirit and scope of the invention, which are defined by the appended claims.

Figure 1:
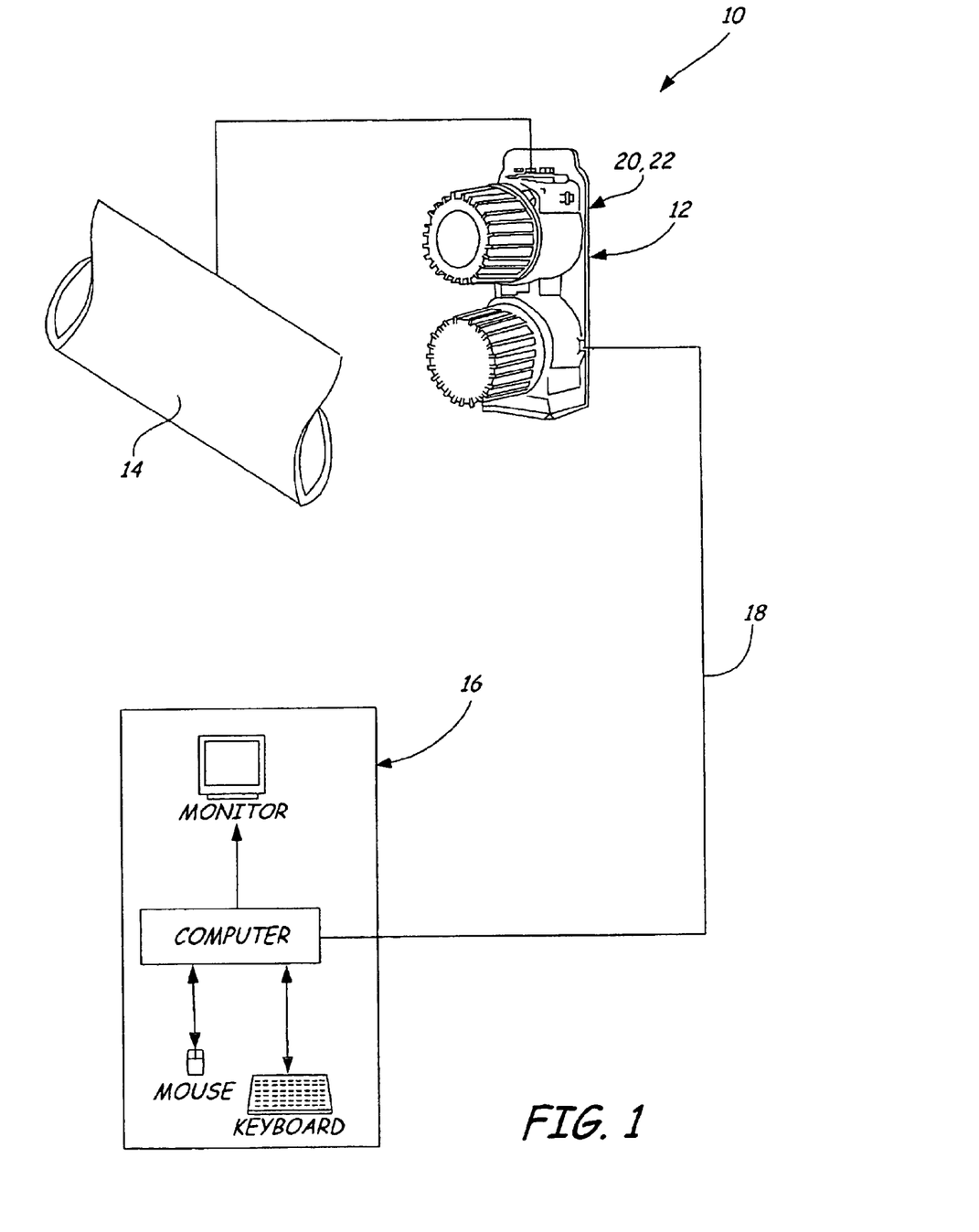
FIG. 1 is a diagrammatic view of an environment of embodiments of the invention.

FIG. 1 is a diagrammatic view of an environment of process control system 10. System 10 includes process analytic system 12 operably coupled to a process fluid container, such as pipe 14, and to computer 16. Process analytic system 12 includes a sample handling system 20 (indicated generally) that is adapted to obtain a sample of process fluid from pipe 14 and convey the sample to a process analyzer 22 (indicated generally) within process analytic system 12. The process analyzer can be a process gas chromatograph, process oxygen analyzer, process combustibles analyzer or any other suitable process analyzer. The process fluid can include a gas, vapor, or liquid. The sample is analyzed within system 12, in accordance with known techniques, to provide a process output. The process output is provided to computer 16 over process communication channel 18, such that the process can be monitored and controlled.

Process communication channel 18 can take a number of forms. For example, system 12 can communicate with computer 16 through an associated infrared input/output port (not shown). Additionally, in some embodiments the output is provided in accordance with a known process industry standard protocol such as the Highway Addressable Remote Transducer (HART®) protocol, or the FOUNDATION™ Fieldbus protocol.

Figure 2:
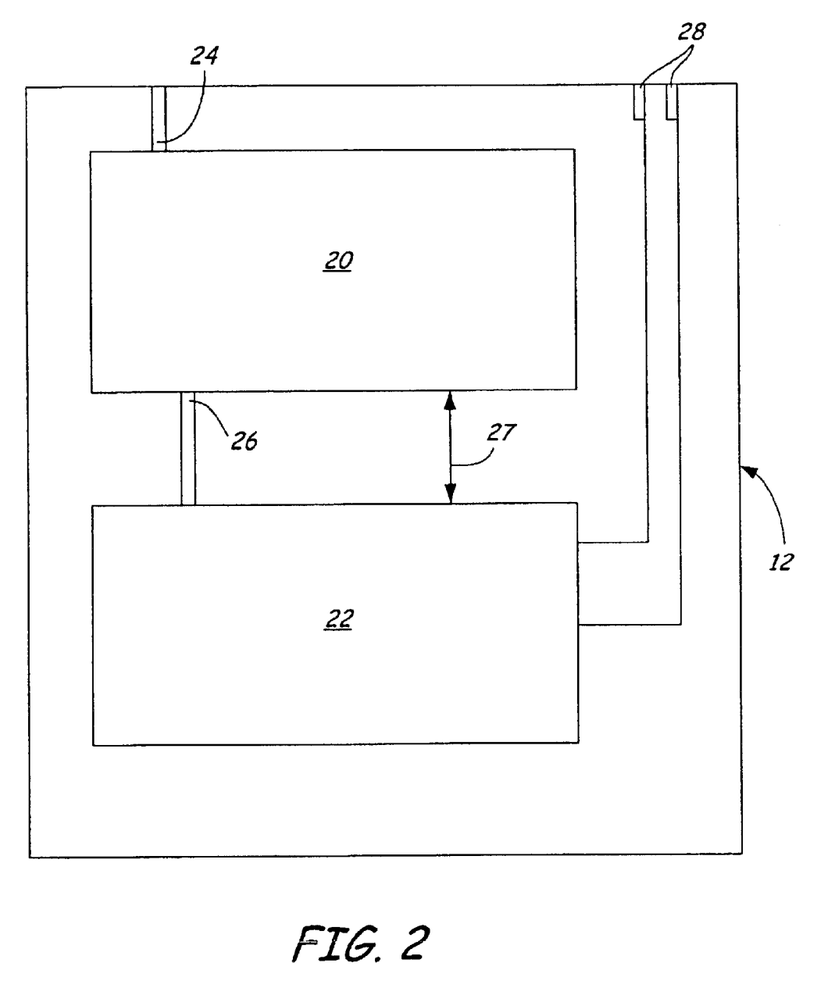
FIG. 2 is a system block diagram of a process analytic system.

FIG. 2 is a system block diagram of process analytic system 12 in accordance with an embodiment of the invention. System 12 includes process sample handling system 20 and process analyzer 22. In some embodiments sample handling system 20 and process analyzer 22 can be disposed within the same transmitter housing.

Sample handling system 20 includes input 24 that is operably coupleable to a process container, such as pipe 14, also referred to as process piping. As will be described in greater detail, sample handling system 20 is adapted to extract a process sample from pipe 14 and convey the process sample to sample output 26. The various components of sample handling system 20 can be constructed from materials that are resistant to the process chemistry as well as process operating temperature. Examples of such material include Type 316 Stainless Steel, and Viton or Kelrez O-rings.

Process analytic system 12 also includes process analyzer 22. Process analyzer 22 is coupled to sample output 26 to receive a process sample from sample handling system 20. Process analyzer 22 is a device that is adapted to analyze the process sample and provide information about the process based upon the analysis. A few examples of process analyzer 22 are a process oxygen sensor, a process gas chromatograph, a process combustibles sensor, or any other appropriate device. Based upon known techniques, analyzer 22 analyzes a process sample received from sample handling system 20, and provides a process analytic system output. The output can be provided through terminals 28 to process communication channel 18.

Analyzer 22 is also operably coupled to sample handling system 20 through digital channel 27, such that digital communication occurs between sample handling system 20 and process analyzer 22. By issuing suitable commands to sample handling system 20, various parameters of system 20, such as flow path, system temperature, system pressure, and sample flow, can be modified. Such modification will be described in greater detail later in the specification. Analyzer 22 can issue such commands based upon diagnostic information related to system 20, analytic information derived from the process sample, or any combination of the two.

The communication between sample handling system 20 and process analyzer 22 can take many forms. For example, analyzer 22 can issue commands to cause sample handling system 20 to clean components within system 20. Additionally, sample handling system 20 can be adapted to provide diagnostic information about one or more of its components to process analyzer 22 such that predictive maintenance of sample handling system 20 is facilitated.

Figure 3:
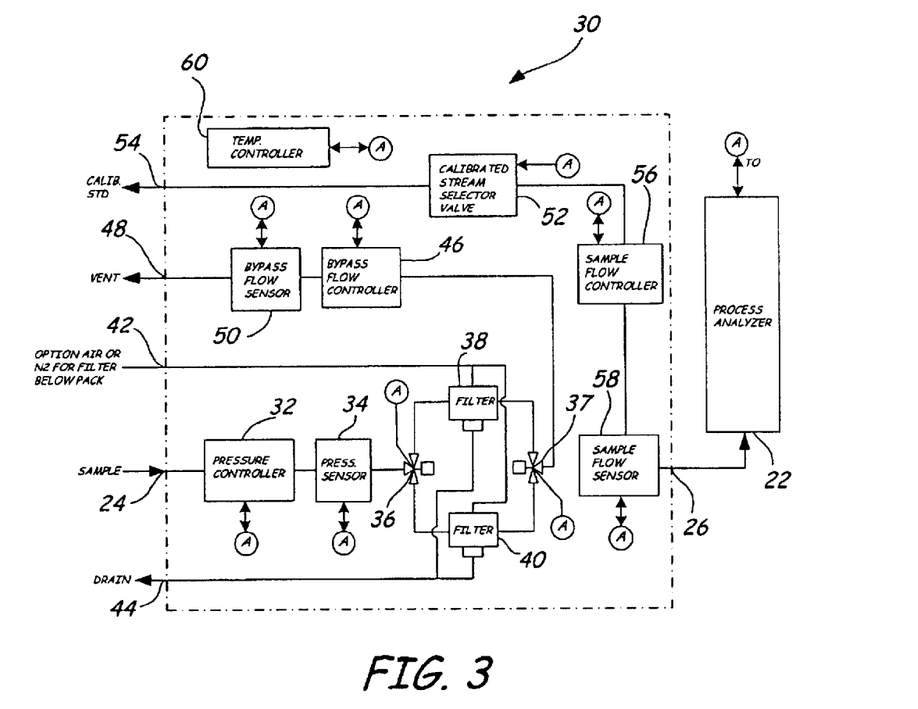
FIG. 3 is a system block diagram of a process analytic system in accordance with one specific embodiment of the invention.

FIG. 3 is a more detailed system block diagram of one example of sample handling system 20. Sample input 24 is coupled to pressure controller 32 in order to control the sample pressure within system 20. Pressure controller 32 is also coupled to process analyzer 22, through digital channel 27 (shown in FIG. 2). The electrical coupling between process analyzer 22 and the various components shown in FIG. 3 is illustrated by the arrow from process analyzer 22 labeled "To (A)" and the various couplings from "(A)" to the components. Pressure controller 32 receives pressurization signals from process analyzer 22 and responsively changes process sample pressure within system 20. Pressure controller 32 can be a known microelectronic pressure reducer, or any other suitable device.

Pressure sensor 34 is coupled to pressure controller 32 and provides a signal related to sample pressure within system 20. Pressure sensor 34 is also coupled to process analyzer 22 such that analyzer 22 receives the sensor signal and takes appropriate action based upon sample pressure within system 20. Pressure sensor 34 is a device that has an electrical characteristic that varies with pressure.

Valves 36, 37 are electrically coupled to process analyzer 22, and in fluidic communication with pressure sensor 34. In the example shown, valves 36, 37 are three-way solenoid valves adapted to selectably direct process sample flow through one of filters 38, 40 in order to filter the process sample. The materials of filters 38, 40 are selected to be resistant to the process sample. For example, each filter 38, 40 can include a filter element constructed from stainless steel. Each filter 38, 40 can be an inline Belston type filter.

Valves 36, 37 and filters 38, 40 are configured such that one of filters 38, 40 can undergo filter blow-back while the other filter continuously filters the process sample. Filters 38, 40 are provided with solenoid valves (not shown) electrically coupled to process analyzer 22 and fluidically interposed between pressurized gas inlet 42 and filters 38, 40. Inlet 42 receives air, nitrogen, or any other suitable gas in order to effect filter blow-back. During filter blow-back, pressurized air or nitrogen is directed through the filter element in order to dislodge any substances that have accumulated upon the filter element. The substances dislodged during blow-back are swept out of the sample handling system through drain 44. Thus, filter cleaning can be effected without interrupting process analysis. In embodiments where online filter blow-back is not desired, one of filters 38, 40 and both of valves 36, 37 can be omitted.

Bypass flow controller 46 is electrically coupled to process analyzer 22 and fluidically coupled to solenoid valve 37. Flow controller 46 is adapted to receive flow control signals from process analyzer 22 and responsively control process sample flow through controller 46. Bypass flow controller 46 can be a micro electronic flow controller. Bypass flow controller 46 controls the amount of process sample flow that is allowed to exit process sampling system 20 through vent 48. Bypass flow controller 46 cooperates with sample flow controller 56 (which will be described later in the specification) to control total process sample flow through sample handling system 20, as well as the ratio of process sample flow vented to process sample flow analyzed.

Bypass flow sensor 50 is electrically coupled to process analyzer 22 and fluidically interposed between bypass flow controller 46 and vent 48. Bypass flow sensor 50 provides a signal to process analyzer 22 based upon process sample flow through sensor 50. Bypass flow sensor 50 can be a micro flow sensor. Additionally flow sensor 50 can be a miniature coriolis mass flow device. Although bypass flow controller 46 and bypass flow sensor 50 are shown and described, separately, they can be embodied within a single flow controller/sensor assembly such as a miniature coriolis mass flow controller assembly, or the Model 5850 S Mass Flow Controller, available from Brooks Instruments, of Hatfield, Pa. Additionally, bypass flow sensor 50 and bypass flow controller 46 can be micromachined from silicon for miniaturization. Bypass flow sensor 50, and sample flow sensor 58 (which will be described later in the specification) provide signals to process analyzer 22 that are based upon sample bypass flow, and sample flow to analyzer 22, respectively. Thus, based upon information from sensors 50, 58, process analyzer 22 can compute total flow through sample handling system 20, or the ratio of process sample flow vented to process sample flow analyzed.

Selector valve 52 is electrically coupled to process analyzer 22 and fluidically coupled to solenoid valve 37, standard port 54, and sample flow controller 56. Based upon a control signal received from process analyzer 22, selector valve 52 provides fluid received from either standard calibration port 54 or through solenoid valve 37 to sample flow controller 56. In this manner, process analyzer 22 can receive a calibration standard for calibration, or a process sample for analysis, as desired. Providing the calibration standard to process analyzer 22 allows the output of analyzer 22 to be compared with a known characteristic of the calibration standard, such as chemical composition, such that error in the process analytic output is reduced, or eliminated.

Sample flow controller 56 is electrically coupled to process analyzer 22, and fluidically coupled to selector valve 52. Sample valve controller 56 can be designed similarly to bypass flow controller 46. Thus, while bypass flow controller 46 controls sample flow to vent 48, sample flow controller 56 controls flow to process analyzer 22. As can be appreciated, bypass flow controller 46 and sample flow controller 56 cooperate to control total sample flow through sample handling system 20.

Sample flow sensor 58 is electrically coupled to process analyzer 22, and fluidically interposed between sample flow controller 56 and sample output 26. Sample flow sensor 58 can be designed identically to bypass flow sensor 50. Sample flow sensor 58 provides a sample flow output to process analyzer 22 that is based upon the amount of process sample flowing from sample outlet 26. Sample flow controller 56 and sample flow sensor 58 can also be embodied in a single assembly such as the Brooks Model 5850 S Mass Flow Controller.

Sample handling system 20 also includes thermal control module 60 coupled to process analyzer 22. Thermal control module 60 includes known thermal control elements such as a temperature sensor and a heater. The temperature sensor is a device that has an electrical property that changes with temperature, such as a resistance temperature device (RTD) or a thermocouple. The temperature sensor is coupled to process analyzer 22 to provide an indication of temperature within sample handling system 20. The heater within thermal control module is a device that converts electricity to heat. The heater is, in thermal communication with at least a portion of the flow path of process sample within sample handling system 20, and is coupled to process analyzer 22 to receive a heating control signal. Thus, thermal control system 60 can maintain the process sample at any appropriate temperature desired by process analyzer 22.

Process analyzer 22 maintains the temperature of sample handling system 20 based upon analysis of the process sample. For example, process analyzer 22 can compute the dew point of the process sample based upon the stream composition, and automatically adjust the temperature of sample handling system 20, via thermal control module 60, based upon the computed dew point. Additionally, process analyzer 22 can be adapted to sense the ambient temperature of sample handling system 20, and ensure that the temperature of system 20 is maintained above the process sample dew point.

As discussed above, process analyzer 22 is coupled to pressure sensor 34, bypass flow sensor 50, and sample flow sensor 58. Additionally, the sum of process sample flowing through bypass flow sensor 50 and sample flow sensor 58 represents total sample flow through system 20. Thus, process analyzer 22 can calculate flow resistance through filters 38, 40 and solenoid valves 36, 37 based upon a measured process sample pressure and total process sample flow. When the flow resistance becomes unacceptably large, process analyzer can command filters 38, 40 such that one filter undergoes filter blow-back while the other continues to filter the process sample.

Process analyzer 22 can be provided with information about each component within sample handling system 20 such that process analyzer can facilitate predictive maintenance of the various components. For example, if solenoid valve 36 has a design lifetime of 100,000 cycles, process analyzer 22 can count the number of actuation signals provided to solenoid valve 36 such that an alarm signal or the like can be provided in advance of the expiration of the designed lifetime of valve 36.

Figure 4:
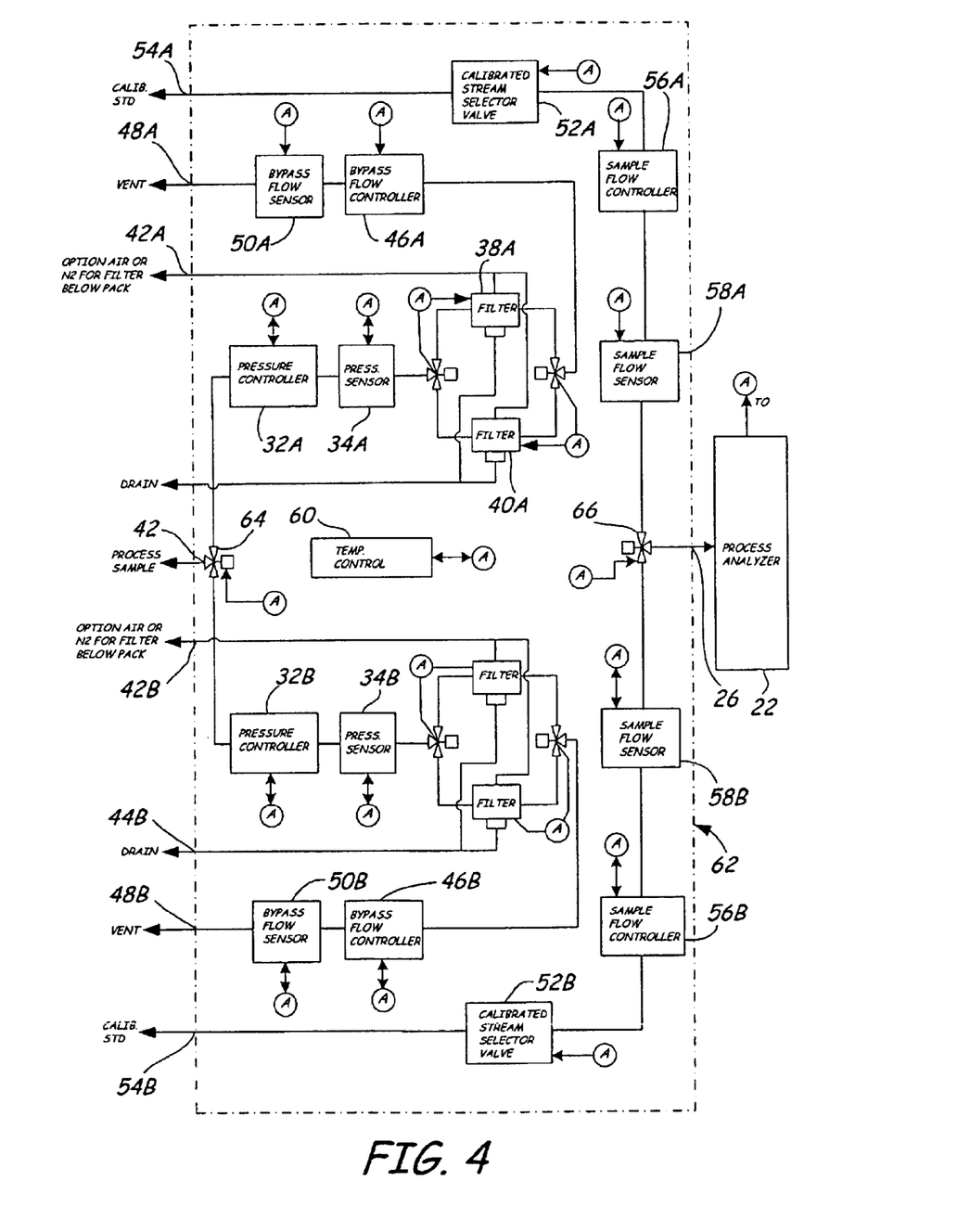
FIG. 4 is a system block diagram of a process analytic system in accordance with another embodiment of the invention.

FIG. 4 is a system block diagram of a process analytic system in accordance with another embodiment of the invention. Sample handling system 62 bears many similarities to sample handling system 20, and like components are numbered similarly. Essentially, sample handling system 62 includes two sample handling modules that are virtually identical to sample handling system 20, mirrored about three way solenoid valves 64 and 66. Additionally, each of the modules can be embodied upon different detachable physical modules such that one module can be removed while the other continues to handle process sample flow. Both of valves 64 and 66 are electrically coupled to process analyzer 22. Thus, process analyzer 22 can command sample handling system 62 to use either of the two sample handling modules.

The configuration illustrated in FIG. 4 provides redundancy, and also facilitates maintenance of system 62 without requiring system 62 to be taken offline. Thus, when process analyzer 22 detects that one of the modules within sample handling system 62 has a problem, or is creating an error, analyzer 22 automatically commands system 62 to switch to the other module. When a malfunction occurs, process analyzer 22 sends appropriate data, such as an alarm, over process communication channel 18 in order to request maintenance upon system 62. When such maintenance is performed, it is not necessary to take the process analytic system offline, since the process sample has been diverted from the malfunctioning module. Although module switching has been described as occurring automatically, it can also be done manually when process analyzer 22 receives a local user input. Such local control can facilitate system maintenance by allowing such maintenance to be conducted without taking the process analytic system offline.

The embodiments illustrated in FIG. 3 and FIG. 4 can be physically embodied within components that are small enough to fit within an industrial transmitter housing. The housing can be made explosion-proof to enhance device safety, or render the device suitable for sensitive applications.

In the embodiments described above, the process analyzer can modify sample handling system parameters such as flow path, sample handling system temperature, sample handling system pressure, bypass flow, and sample flow to the analyzer. Such control allows software in the process analyzer to facilitate the setup of the sample handling system. Moreover, the process analyzer can continuously monitor characteristics of the process sample or diagnostic information related to the sample handling system, and adjust any of the various parameters of the sample handling system.

What is claimed is:

1. A process analytic system, comprising:
   a sample handling system having a sample output, and a sample input, the sample input being couplable to a process container to extract a sample from the container and convey the sample to the sample output;
   a process analyzer coupled to the sample output of the sample handling system, and adapted to analyze the sample to provide an analytical output based upon a characteristic of the sample; and
   wherein the process analyzer is operably coupled to the sample handling system to modify at least one sample handling parameter based upon diagnostic information related to the sample handling system.

2. The system of claim 1, wherein the process analyzer is selected from the group consisting of process gas chromatograph, process oxygen analyzer, and process combustibles analyzer.

3. The system of claim 1, wherein the process analyzer is electrically coupled to the sample handling system.

4. The system of claim 1, wherein the analyzer is adapted to receive digital diagnostic information from the sample handling system.

5. The system of claim 1, wherein the sample handling system further comprises:
   a first calibration standard input adapted to receive a first calibration standard;
   a first pressure controller operably coupled to the sample input and adapted to provide a first pressure-regulated sample output;
   a first pressure sensor having a first pressure sensor output, and a first pressure sensor input, the first pressure sensor input coupled to the first pressure-regulated sample output, and adapted to provide a first sample pressure signal based upon a pressure measured at the pressure-regulated sample output;
   a first filter coupled to the first pressure sensor output to provide a first filtered sample output;
   a first selector valve operably coupled to the first calibration standard input and the first filtered output to selectably couple one of the first filtered output and the first calibration standard input to a first selector valve output;
   a first sample flow controller coupled to the first selector valve output to provide a first flow-regulated sample output;
   a first flow sensor having a first flow sensor input coupled to the first flow-regulated sample output, and a first flow sensor output operably coupled to the sample output, and wherein the first flow sensor is adapted to provide a first flow signal based upon sample flow through the flow sensor.

6. The system of claim 5, and further comprising:
   a first bypass flow controller having a first bypass flow controller output, and a first bypass flow controller input, the first bypass flow controller input operably coupled to the first filtered sample output; and
   a first bypass flow sensor operably interposed between the first bypass flow controller output and a vent, and wherein the first bypass flow sensor is adapted to provide a bypass flow sensor signal to the process analyzer based upon bypass flow through the bypass flow sensor.

7. The system of claim 5, wherein the first filter is operably couplable to a pressurized source of gas for filter blow-back.

8. The system of claim 7, wherein the gas is selected from the group consisting of air and nitrogen.

9. The system of claim 7, wherein at least the first pressure sensor, first bypass flow sensor and first sample flow sensor are operably coupled to the process analyzer, and the process analyzer is adapted to calculate flow resistance through the first filter and automatically issue a filter blow-back signal when flow resistance through the first filter exceeds a threshold.

10. The system of claim 5, wherein the first filter includes a stainless steel filter element.

11. The system of claim 5, and further comprising a second filter disposed in parallel with the first filter such that one of the first and second filters can undergo filter blow-back while the other filters the sample.

12. The system of claim 5, and further comprising:
    a second calibration standard input adapted to receive a second calibration standard;
    a second pressure controller operably coupled to the sample input and adapted to provide a second pressure-regulated sample output;
    a second pressure sensor having a second pressure sensor output, and a second pressure sensor input coupled to the second pressure-regulated sample output, and adapted to provide a second sample pressure signal based on a pressure measured at the second pressure-regulated sample output;
    a second filter coupled to the second pressure sensor output to provide a second filtered sample output;
    a second selector valve operably coupled to the second calibration standard input and the second filtered output to selectably couple one of the second filtered output and the second calibration input to a second selector valve output;
    a second sample flow controller coupled to the second selector valve output to provide a second flow-regulated sample output;
    a second flow sensor having a second flow sensor input coupled to the second flow-regulated sample output, and a second flow sensor output operably coupled to the sample output, and wherein the second flow sensor is adapted to provide a second flow signal to the process analyzer based upon sample flow through the second flow sensor.

13. The system of claim 12, wherein the analyzer is adapted to selectably receive a sample through one of the first and second flow sensor outputs based upon diagnostic information related to the sample handling system.

14. The system of claim 12, wherein the sample handling system and the process analyzer are disposed within a single transmitter housing.

15. The system of claim 1, wherein the sample handling system and the process analyzer are disposed within a single transmitter housing.

16. The system of claim 1, and further comprising a thermal control system disposed within the sample handling system and operably coupled to the process analyzer to maintain the sample handling system at a selected temperature.

17. The system of claim 16, wherein the selected temperature is related to process sample dew point.

18. The system of claim 17, wherein the process sample dew point is calculated by the process analyzer.

19. The process analytic system of claim 1 wherein the at last one sample handling parameter includes sample pressure.

20. The process analytic system of claim 1 wherein the at least one sample handling parameter includes sample flow.

21. The process analytic system of claim 1 wherein the at least one sample handling parameter includes a ratio of sample flow to vent.

22. The process analytic system of claim 1 wherein the sample handling parameter includes bypass flow.

23. The process analytic system of claim 1 wherein the at least one sample handling parameter includes total sample flow.

24. A process analytic system, comprising:

a sample handling system having a sample output, and a sample input, the sample input being couplable to a process container, and wherein the sample handling system is adapted to extract a sample from the container and convey the sample to the sample output;

a process analyzer coupled to the sample output of the sample handling system, and adapted to analyze the sample to provide an analytical output based upon a characteristic of the sample; and wherein the process analyzer is operably coupled to the sample handling system to communicate digitally with the sample handling system.

* * * * *

UNITED STATES PATENT AND TRADEMARK OFFICE
CERTIFICATE OF CORRECTION

PATENT NO. : 6,846,458 B1
DATED : January 25, 2005
INVENTOR(S) : Staphanos It is certified that error appears in the above-identified patent and that said Letters Patent is hereby corrected as shown below:

Column 9,
Line 4, "last" should be -- least --

Signed and Sealed this

Twenty-first Day of June, 2005

JON W. DUDAS
*Director of the United States Patent and Trademark Office*